United States Patent [19]
Kupperblatt

[11] Patent Number: 5,882,677
[45] Date of Patent: Mar. 16, 1999

[54] IONTOPHORETIC PATCH WITH HYDROGEL RESERVOIR

[75] Inventor: Gary B. Kupperblatt, Flanders, N.J.

[73] Assignee: Becton Dickinson and Company, Franklin Lakes, N.J.

[21] Appl. No.: 941,746

[22] Filed: Sep. 30, 1997

[51] Int. Cl.[6] ........................................... A61K 9/70
[52] U.S. Cl. ..................... 424/449; 424/443; 424/444; 424/447; 604/304; 604/890.1; 604/892.1
[58] Field of Search ........................ 424/443, 444, 424/447, 449; 604/304, 890.1, 892.1

[56] References Cited

U.S. PATENT DOCUMENTS

| | | | |
|---|---|---|---|
| 4,927,408 | 5/1990 | Haak et al. | 604/20 |
| 5,084,008 | 1/1992 | Phipps | 604/20 |
| 5,203,768 | 4/1993 | Haak et al. | 604/20 |
| 5,250,022 | 10/1993 | Chien et al. | 604/20 |
| 5,362,308 | 11/1994 | Chien et al. | 604/20 |

*Primary Examiner*—Jose'G. Dees
*Assistant Examiner*—Michael A. Williamson
*Attorney, Agent, or Firm*—Susan A. Capello; Royal N. Ronning, Jr.; David T. Banchik

[57] ABSTRACT

An improved hydrogel reservoir for use in two-compartment iontophoretic patches is described. The hydrogel reservoir contains a water soluble polyelectrolyte and a fluid. The reservoir may also contain a matrix forming material such as polyvinylpyrrolidone. A preferred water-soluble polyelectrolyte is sodium polystyrene sulfonate.

9 Claims, 3 Drawing Sheets

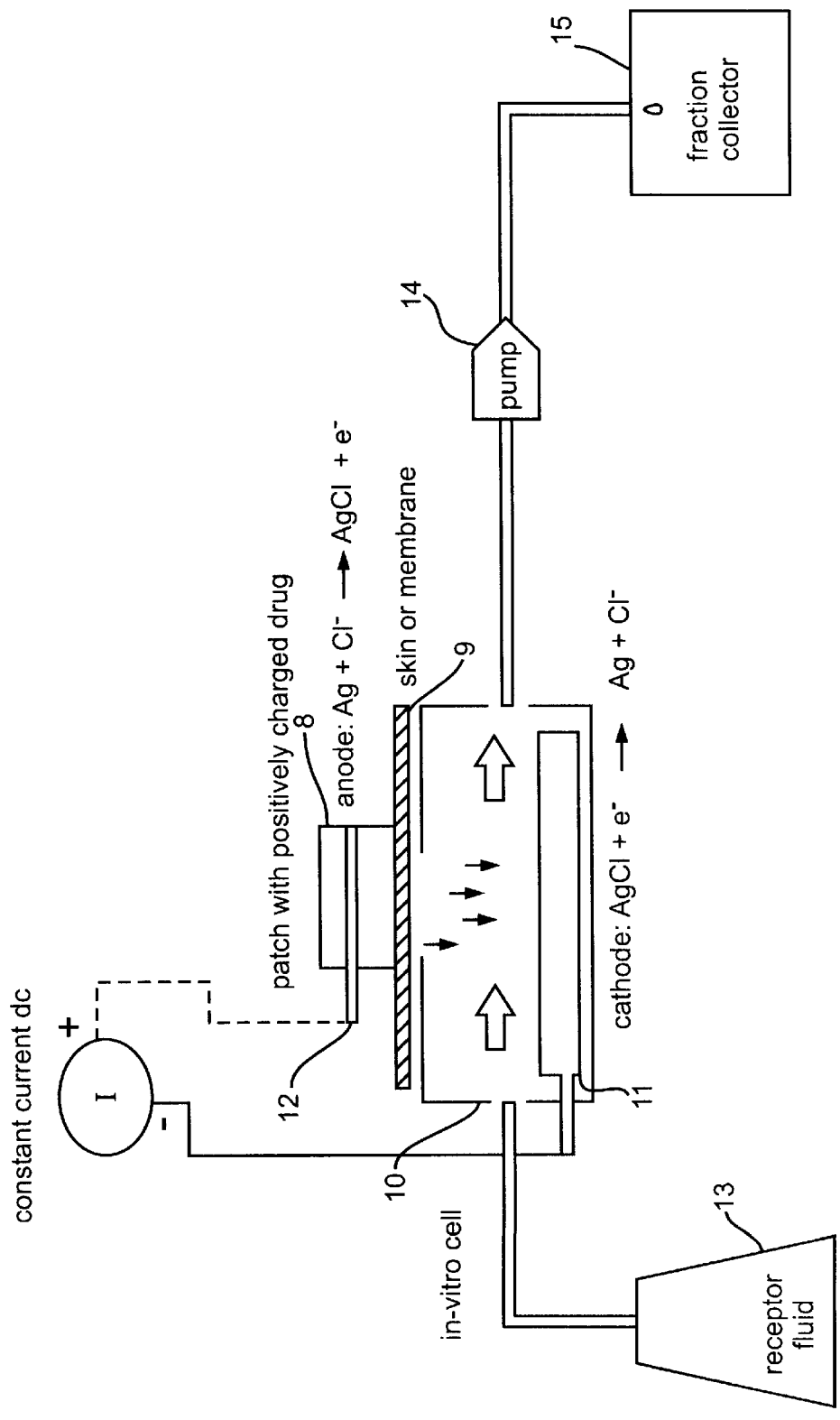
FIG-2 Anodal Iontophoretic Drug Delivery - In vitro Cell Platform

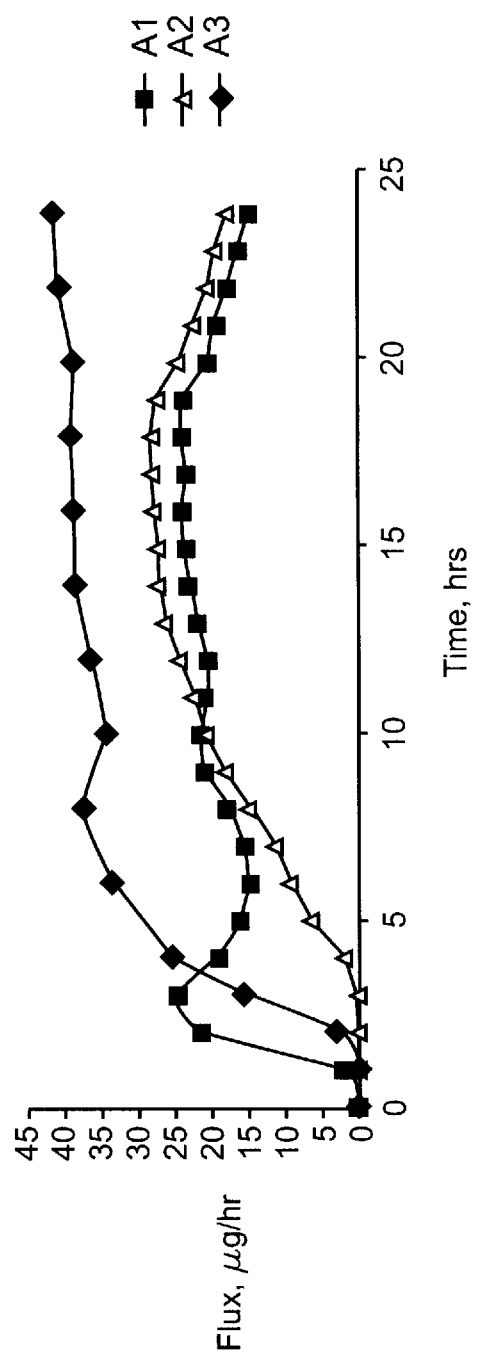
FIG-3 In-Vitro Delivery of Drug Compound

IONTOPHORETIC PATCH WITH HYDROGEL RESERVOIR

BACKGROUND OF THE INVENTION

FIELD OF THE INVENTION

The present invention relates to an iontophoretic patch for the transdermal delivery of drugs, with an improved hydrogel reservoir.

Administration of medicaments using iontophoresis is known. Simply defined, iontophoresis is the introduction by means of electric current, of ions of soluble salts into the tissues of the body for therapeutic purposes. In presently known iontophoretic devices, at least two electrodes are used. Both of these electrodes are positioned to be in intimate electrical contact with some portion of the skin of the body. One electrode, called the active or donor electrode, is the electrode from which the ionic substance, medicament, drug precursor or drug is delivered into the body by iontophoresis. The other electrode, called the counter or return electrode, serves to close the electrical circuit through the body. In conjunction with the patient's skin contacted by the electrodes, the circuit is completed by connection of the electrodes to a source of electrical energy, e.g., a battery. For example, if the ionic substance to be delivered into the body is positively charged, i.e. a cation, then the anode will be the active electrode and the cathode will serve to complete the circuit. If the ionic substance to be delivered is negatively charged, i.e. an anion, then the cathode will be the active electrode and the anode will be the counter electrode.

Alternatively, both the anode and cathode may be used to deliver drugs of opposite charge into the body. In such a case, both electrodes are considered to be active or donor electrodes. For example, the anode can deliver a positively charged ionic substance into the body while the cathode can deliver a negatively charged ionic substance into the body.

It is also known that iontophoretic delivery devices can be used to deliver an uncharged drug or agent into the body. This is accomplished by a process called electroosmosis. Electroosmosis is transdermal flux of a liquid solvent (e.g., the liquid solvent containing the uncharged drug or agent) which is induced by the presence of an electric field imposed across the skin by the donor electrode. As used herein, the terms "iontophoresis" and "iontophoretic" apply equally to electrically powered devices which deliver charged/ionic agents by iontophoresis as well as to electrically powered devices which deliver uncharged/nonionic agents by electroosmosis.

In the typical iontophoretic patch, a matrix of reservoirs to hold the drug or medicament, or beneficial agent is provided. A reservoir can be of any material adapted to absorb and hold a sufficient quantity of liquid therein in order to permit transport of agent therethrough by iontophoresis. Preferably, a matrix of reservoirs is used, which is composed at least in part of a hydrophilic polymer.

In order to conduct electrical current the reservoirs must be sufficiently hydrated to allow ions to flow therethrough. In most cases the liquids used to hydrate the matrices of the reservoirs will be water, but other liquids can also be used to activate the matrices of the reservoirs.

The combination of water soluble polymer and water or liquid results in the reservoir containing a hydrogel. Electrical current is applied to the reservoir by means of a current distributing member. This member can take the form of a metal plate, a foil layer, a screen or a dispersion of particles.

Use of sacrificial current distributing members which are oxidized or reduced during drug delivery are preferred. However, such devices produce ions, such as silver ions, which cannot be permitted to be transferred to the skin due to adverse affects. Nor can a significant build-up of ions be permitted because the efficiency of the iontophoresis device may be impeded due to competition with the drug ion.

Therefore it is necessary for the reservoir also to contain a counter-ion to react with the electrochemically generated ion. However, many drug salts do not possess the proper ion for reacting with the electrochemically generated ion. For example, in some instances, water soluble salts would be produced, which would remain in their ionized state in the reservoir. Therefore, it is important to provide a counter-ion in the reservoir which can effectively eliminate the ion generated by the electrode.

Since the drug to be delivered is also charged, precautions must be taken to prevent the drug from coming into contact with counter-ions which are incorporated to eliminate the ion generated by the electrode. Methods of accomplishing this are known in the art. A two compartment model is typically used, comprising a drug reservoir which must be isolated from the second reservoir containing the active electrode by a membrane that prevents direct contact between the drug and the ion exchange media.

Membranes, typically size exclusion membranes, are used to separate the two reservoir compartments. The membrane must be selected to prevent the drug ion from migrating into the reservoir containing the active electrode, and also to prevent the ion exchange means from drifting into the drug reservoir. An example of such a two compartment device is shown in FIG. 1. A two compartment reservoir 1, is divided into an upper reservoir 2 containing an active electrode 3. The reservoirs are situated in a foam ring 6. The upper reservoir is separated from a lower reservoir 4 by a separator membrane 5. In this instance the drug is stored in the lower reservoir. The bottom of the lower reservoir is sealed by a release liner 7, which is removed prior to application of the iontophoretic device to a patient. Examples of other two compartment membranes may be found in Haak, U.S. Pat. No. 4,927,408 and Phipps, U.S. Pat. No. 5,084,008.

In Phipps, it is the drug containing reservoir which is equipped with the counter ion. In one embodiment, this is accomplished by constructing an electrode having a conductive, current distributing member; means for coupling the current distributing member to a source of electrical current; a reservoir containing an ionic or ionizable drug; an ion source layer in intimate contact with the current distributing member; and a layer of selectively permeable material applied to the ion source layer which is between the current distributing member and the reservoir. Examples of ion source layers include salt layers, ion exchange resins or chelating agents. Also useful are salts in thin hydrogel material or a substantially dehydrated layer which would absorb a solvent. The selectively permeable material is capable of separating materials by charge and/or size. The construction of this device is complex, involving many different layers, thus increasing the cost and time for their manufacture.

Haak discloses a construction where the drug reservoir is in contact with a membrane, including a hydrogel, which is loaded with an ion exchange resin or a chelating agent. However, such a device brings the drug into contact with ion exchange media, such as a membrane or resin, and this can lead to some portion of the drug becoming immobilized. Further, restricting the ion exchange capacity of the device to a thin membrane, rather than a large volume of material, limits its ion exchange capacity.

Phipps U.S. Pat. No. 5,423,739 discloses a two layer iontophoretic device, wherein the top layer is referred to as the carrier layer and the bottom layer is the skin-contacting layer. The skin contacting layer contains an ionic polymer component. In Phipps, the carrier layer includes the drug or active agent, and few or no mobile ionizable substances. In one embodiment, the mobile ions of the hydrogel in the skin contacting layer have a charge opposite from that of the ionized active agent. This means that the ionized active agent and the polymer backbone have the same charge. The two layers are separated by an impermeable carrier and the device only becomes active when this impermeable barrier is breached. Once the impermeable barrier is broken, the ionized active agent and the mobile counter ions are in direct contact with each other. This contact can lead to unwanted interaction between these two elements and adversely affect drug delivery.

Phipps also suggests that the relatively small counter ion of the ionomeric component in the skin contacting layer can be selected to interact with the electrochemically generated species at the anode or the cathode. However, this arrangement relies on the mobile counter ions being able to come into contact with the electrochemically generated ions in a very complex matrix system. Due to the complexities of various hydrogel systems, one cannot always be assured that the mobile counter ions will encounter and react with the electrochemically generated ions. Further, the unwanted interactions between the ionized active agent and the mobile counter ion also exist in this arrangement.

Additionally, Phipps shows examples where the active agent and the ionic polymer backbone are oppositely charged. However, in these instances, the active agent and the ionic polymer are in direct contact with each other in order to convert the active agent to a cationic state.

Additionally, the reservoirs containing the active electrode have been known to include water-insoluble, cross-linked ion-exchange resins which serve to bind the ion generated during the iontophoretic process. An example of the use of a non-water soluble ion-exchange resin in a iontophoretic patch reservoir is found in Chien, et al., U.S. Pat. No. 5,250,022.

Ion-exchange resins, which are included in the hydrogel in the reservoir in the prior art, such as those disclosed in Chien, result in the hydrogel reservoir having a non-uniform consistency. The resins often settle out of the matrix. Very high concentrations of ion exchange resin at the bottom of the reservoir can hinder ion mobility, which can seriously affect the operation of the iontophoretic patch.

Uniform reservoirs are also difficult to achieve when processing the ion-exchange resins due to the fact that the cross-linked particles behave as a filler, so viscosity increases hyperbolically with particle concentration. The matrix can often become very dough-like in preparation. This results in production difficulties, and consequently increases the cost of the product, due to lengthy production times and a high rejection rate of finished product. The high viscosity also limits formulation possibilities in designing the drug reservoir.

Ion-exchange membranes, on the other hand, are physical barriers which are not only susceptible to flaws, they can also be damaged, thus potentially greatly diminishing their effectiveness.

It is therefore an object of this invention to produce a hydrogel reservoir matrix for a two compartment iontophoretic patch which is homogeneous and not susceptible to separation.

It is another object of this invention to provide a hydrogel reservoir matrix for a two compartment iontophoretic device which can be processed easily, and which does not have an excessive viscosity.

Yet another object of this invention is a hydrogel reservoir matrix for a two compartment iontophoretic patch which is not dependent on a thin physical barrier for ion exchange.

Higher ion exchange capacity per unit volume in a hydrogel reservoir matrix for an iontophoretic patch is also a desired object of this invention.

Increased reliability of the capture of electrochemically generated ions is another feature of the present invention.

SUMMARY OF THE INVENTION

The present invention solves the problems of the prior art hydrogel matrices by using water soluble polyelectrolytes as a constituent of the hydrogel reservoirs in two compartment iontophoretic patches. These polyelectrolytes are selected to have a fixed counter-ion on the polymer chain which can bind a suitably charged ion (i.e. ion exchange). The most common ion for which such an interaction is useful is the silver ion generated at a silver electrode during iontophoresis. The polyelectrolyte is chosen so that it is miscible with or even soluble with the polymers that make up the hydrogel phase in the hydrogel reservoir. In such a case, the polyelectrolyte becomes dispersed on a very small scale level.

BRIEF DESCRIPTION OF THE DRAWINGS

FIG. 2 is a schematic representation of anodal iontophoretic drug delivery in an in vitro cell.

FIG. 3 is a graph showing the amount of drug delivery as a function of time using the iontophoretic patch of the present invention.

DETAILED DESCRIPTION OF THE INVENTION

Figure 1:
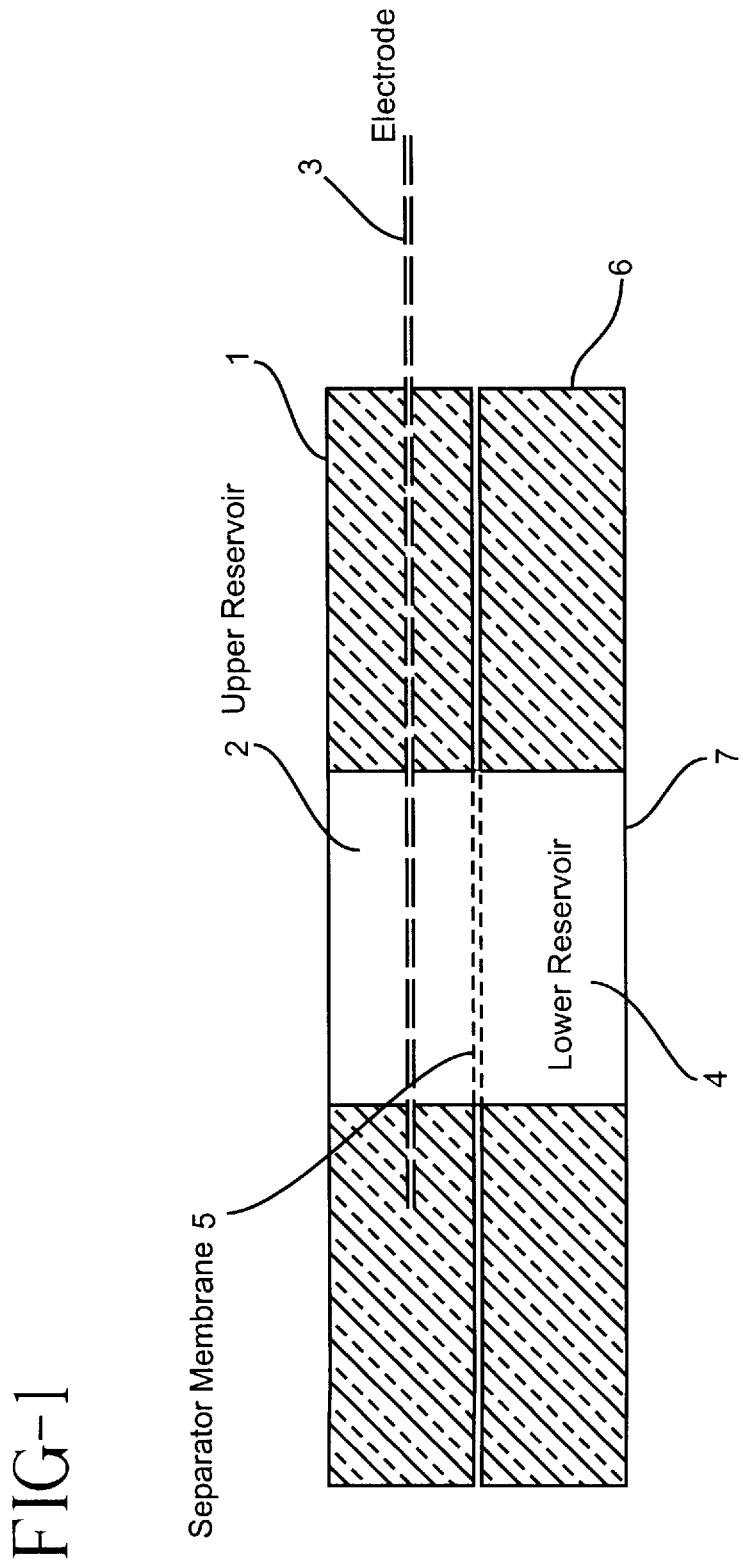
FIG. 1 is a diagram of a two-compartment iontophoretic patch.

The present invention is directed to an improvement in the hydrogel reservoir of an iontophoretic patch. The improvement resides in the use of a water soluble polyelectrolyte in the reservoir to bind ions generated during electrophoresis. By relying on a polymer to bind these ions in such a complex system, rather than small mobile ions, the dependability of the system is enhanced.

The reservoir itself must be hydrated. Moreover, the reservoir is in the form of a matrix. Most preferably, the matrix of reservoirs is composed of a matrix-forming material. This matrix forming material is, at least in part, composed of a hydrophilic polymer material. Both natural and synthetic hydrophilic polymers may be used. Suitable hydrophilic polymers include polyvinylpyrrolidones, polyvinyl alcohol, polyethylene oxides such as Polyox® manufactured by Union Carbide Corp.; Carbopol® manufactured by BF Goodrich of Akron, Ohio; blends of polyoxyethylene or polyethylene glycols with polyacrylic acid such as Polyox® blended with Carbopol®, polyacrylamide, Klucel®, cross-linked dextran such as Sephadex (Pharmacia Fine Chemicals, AB, Uppsala, Sweden); Water Lock® (Grain Processing Corp., Muscatine, Iowa) which is a starch-graft-poly(sodium acrylate-co-acrylamide)polymer; cellulose, derivatives such as hydroxyethyl cellulose, hydroxypropylmethylcellulose, low substituted hydroxypropylcellulose, and cross-linked Na-carboxymethylcellulose such as Ac-Di-Sol (FMC Corp., Philadelphia, Pa.); hydrogels such as polyhydroxyethyl methacrylate (National Patent Development Corp.); natural gums, chitosan, pectin, starch, guar gum, locust bean gum, and the like, along with blends thereof. Of these, polyvinylpyrrolidones are preferred.

In order to conduct electrical current, the reservoirs must be sufficiently hydrated to allow ions to flow therethrough. In most cases the liquid used to hydrate the matrices of the reservoirs will be water, but other non-aqueous liquids, can also be used to "hydrate" (i.e., activate) the matrices of the reservoirs. In the typical case where the hydrating liquid is water, the matrices of the reservoirs will be at least partly composed of a hydrophilic material such as a hydrophilic polymer, a cellulose sponge or pad or other water retaining material. Most preferably, the matrices of the reservoirs will be at least partly composed of a hydrophilic polymer of the type described hereinbefore.

The present invention relies on the use of water soluble polyelectrolytes. The term polyelectrolyte denotes a class of macromolecular compounds, which, when dissolved in a suitable polar solvent, such as water, spontaneously acquire or can be made to acquire a large number of elementary charges distributed along the macromolecular chain. See Concise Encyclopedia of Polymer Science and Engineering, J. I. Kroschwitz (Ed.), 1990, pp. 788–93.

The water soluble polyelectrolytes used in the present invention are selected so that the fixed ion on the polymer chain can bind a suitably charged ion generated by the electrode during iontophoresis. The polyelectrolyte is chosen so that it is miscible with or even soluble with the polymers that make up the hydrogel phase in the matrix.

Another important characteristic of the polyelectrolyte selected is that it must be medically acceptable. For example, a polyelectrolyte with Hg or Ag ions would not be acceptable. Further, the polyelectrolyte must be medical grade, so that no harmful solvents or residual monomers are incorporated into the iontophoretic patch.

The polymer selected also should not be cross-linked, and should have a molecular weight of about 1,000 or greater. Polyelectrolytes with strongly ionic groups such as sulfonates, carboxylates and phosphates may be used. Examples of polyelectrolytes which are suitable for use in the present invention are the high molecular weight cations cholestyramine, dextran carbonates, aminated styrenes, polyvinylimine, polyethyleneimine, poly(vinyl 4-alkylpyridinium), and poly(vinylbenzyltrimethyl ammonium). Suitable high molecular weight anions include polymethacrylates, polystyrene sulfonates, hyaluronate, alginate, dextran sulfonates, acrylamido methyl propane sulfonates ("poly-AMPS"), hydroxy ethyl methacrylate ("poly-HEMA"), and sodium polystryene sodium sulfonate ("NaPSS"). The anionic compounds are preferred, with poly-AMPS, poly-HEMA and NaPSS being more preferred. The most preferred water soluble polyelectrolyte is NaPSS, which is available under the trademark Kayexalate from Spectrum Chemical Mfg. Corp. This polyelectrolyte is the sodium form of a sulfonated divinylbenzene styrene copolymer.

Interestingly, use of a macroscopic, cross-linked polyelectrolyte composition with the same chemical identity as NaPSS, results in a hydrogel matrix having the problems noted earlier. More specifically, Amberlite IRP-69 is a pharmaceutical grade cation exchange resin available from Rohm and Haas Company. It is supplied as a dry, fine powder and is derived from a sulfonated copolymer of styrene and divinylbenzene. Combination of 15% of this resin with 15% polyvinylpyrrolidone and 70% water to form a hydrogel matrix for iontophoretic drug delivery presents rheological problems. If the total solids content is above about 35%, the mixture becomes highly viscous and difficult to process. If the amount of PVP is too low, the ion-exchange resin will settle out of the mixture. That means that for some drugs, it is not possible to add enough ion exchange resin without making the reservoir very large. The drug reservoir cannot become too large because that increases the dilution of the drug and tends to decrease the dose efficiency of the patch.

Additionally, the formulations containing the ion-exchange resin frequently lack sufficient tackiness. Tackiness is an important feature of a hydrogel reservoir because a non-sticky hydrogel can separate from the electrodes and cause failure of the device.

In contrast, a similar reservoir made using the water soluble NaPSS polyelectrolyte of the present invention is sufficiently tacky to avoid problems of separation. Moreover, the composition is not too viscous, does not separate on standing and is easier to process.

The amount of polymer or other substance used to form the reservoir matrix can vary, but is typically about 1 to about 50%.

The amount of water soluble polyelectrolyte contained in the hydrogel matrix reservoir can be from 1–100% of the matrix, with 10–100% being the preferred range.

The higher range of water soluble polyelectrolyte is suitable in the instance where the polyelectrolyte is capable of forming a gel by itself.

Any drug capable of iontophoretic delivery may be used in the present invention. For example drugs used in pain management, such as morphine, sufentanil, remifentanil, Ketorolac®, butorphanol, fentanyl, hydromorphone, oxymorphone and buprenorphine are useful in the invention.

Anti-emetics such as ondansetron, granisetron, and metoclopramide may be used.

Migraine treatments including dihydroergotamine, 311C naratriptan and sumatriptan may also be used.

Drugs which may be classified as peptides are also capable of iontophoretic delivery. Examples of such compounds include calcitonin used to treat osteoporosis, octreotide, which is used to counteract the effects of growth hormone and enkephalins, endorphins, and analogs for pain management.

Other drugs which would be useful in the present invention include, but are not limited to, analgesics, antithrombotics, anticonvulsants, antidepressants, antiinflammatory agents, antiobesity agents and antipsychotics. Other classes of drugs which would find utility in the present invention are known to those familiar with iontophoretic drug delivery.

The two compartments of the iontophoretic patch can be separated by a number of methods disclosed in the prior art, as previously described. In the present invention, permeable, size exclusion membranes are the preferred means of separating the reservoir containing the active electrode and the drug reservoir. The size exclusion membrane must be capable of preventing drug molecules from diffusing into the reservoir containing the active electrode, and also of preventing ion exchange polyelectrolytes from diffusing down into the drug reservoir, yet permit the passage of small ions necessary for the iontophoretic process to take place. The drug molecules are usually much smaller than the ion exchange polyelectrolyte, and are the limiting factor in membrane selection. As an example of a size exclusion membrane which may be used in the present invention, YCO-5, available from Amicon is suitable. YCO-5 is a membrane consisting of cellulose acetate. Of course, any size exclusion membrane which meets the performance criteria outlined above may be used.

The iontophoretic delivery device of the present invention is preferably flexible enough to conform to contours of the body. While not limited to any particular size or shape, the device typically is about two or three inches long, about one and one-half inches wide, and has a thickness of approximately one-quarter of an inch. The combined skin-contacting areas of electrode assemblies can vary from less than 1 cm$^2$ to greater than 200 cm$^2$. The average device however, will have electrode assemblies with a combined skin-contacting area within the range of about 5 to 50 cm$^2$. As constructed, electrode assemblies are electrically isolated from each other until the device is applied to the human body, whereupon a circuit through the human tissue is completed between the electrode assemblies.

The beneficial agent or drug, in the case of the donor electrode reservoir and the electrolyte salt in the case of the counter electrode reservoir may be added to the drug reservoir matrix either at the time of manufacture of the device or at the time of use of the device. For example, when the drug or electrolyte is added to the drug-containing reservoir matrix at the time of manufacture of the device, blending of the drug or electrolyte with the drug reservoir matrix components can be accomplished mechanically either by milling, extrusion, or hot-melt mixing. The resulting dry state reservoirs may then be prepared by solvent casting, extrusion or by melt-processing, for example. In addition to the drug and polyelectrolyte, the reservoirs may also contain other conventional materials such as dyes, pigments, inert fillers, and other excipients.

On the other hand, the reservoirs may be manufactured with no drug or polyelectrolyte. In drug a case, the drug and polyelectrolyte can be added to the reservoirs, by adding a solution of the drug and a solution of the polyelectrolyte to the appropriate reservoir matrix and compartment at the time of use.

Other ingredients such as antimicrobial agents and antioxidants may also be beneficially included in the hydrogel reservoir of the present invention.

EXAMPLE 1

Ingredients

15% BASF K90F polyvinylpyrrolidone

15% Kayexalate® USP grade Sodium Polystyrene Sulfonate (NaPSS)

1% Nipastat Phenonip® (an antimicrobial preservative)

0.09% NaCl

Balance water

This formulation was mixed to dissolve the solid components.

Three compositions with the above formulations were prepared. They were designated A1, A2, and A3.

The compositions described above were placed into 2 cm$^2$ anode patches, whose construction is described below. After each composition was in place in the upper compartment of the patch, it was irradiated in situ with a high energy electron beam to crosslink the composition. Naturally, the higher the dose of energy applied, the greater the resulting degree of crosslinking.

Composition A1 received 2.3 mrad of radiation. Compositions A2 and A3 both received 1 mrad of radiation each.

Subsequently, the patches containing compositions A1, A2 and A3 were evaluated in an in vitro system to determine if the resulting patch was able to meet its intended function.

The patches were made using a two-compartment model, as shown schematically in FIG. 1. The lower, drug containing reservoir is made using a rigid, open-celled polyethylene, hydrophilic foam, available from Porex Technologies Corp., Fairburn, Ga., as part no. 4896. A separator membrane, such as Amicon's YCO-5 with a 500 molecular weight cut-off, is placed on the upper side of the lower reservoir. The bottom of the lower reservoir is sealed with an adhesive liner. The upper reservoir is fabricated using strips of adhesive coated polyethylene foam, such as those available from Avery Dennison, Specialty Tapes Division. A one eighth inch thick foam is used. Die cut holes are made in the foam to permit the introduction of the electrode. Delker Corporation supplies the silver mesh used for the electrode, part number 6AG-10-077.

The reservoirs can be filled via pipette or by syringe. In the in vitro experiments performed using the above hydrogel formulation, the drug reservoirs contained a proprietary, cationic peptide drug having a molecular weight of about 600 which functions as a growth hormone releasing peptide (GHRP). A composition containing this GHRP was placed in the lower reservoir and was prepared using the following ingredients:

1.5 gram peptide drug, radioactively labeled 0.32 gram glacial acetic acid 1.5 gram glycerine 1.68 gram deionized water The above ingredients were mixed to yield a formulation having a drug concentration of 100 mg/ml. The acetic acid is present to ionize the peptide.

Drug delivery in an in vitro model was used to evaluate the performance of the patch containing the hydrogel composition of Example 1. The in vitro model is shown schematically in FIG. 2, and is generally known in the art. (W. J. Addicks, G. L. Flynn and N. Weiner, "Validation of a Flow-through Diffusion Cell for use in Transdermal Research", *Pharmaceutical Research*, vol.4, 1987, pp.337–341). According to FIG. 2, an iontophoretic patch 8, as described above, was placed on a skin or membrane 9, such as excised pig skin. Excised pig skin can be prepared according to known methods, including those described in Kligman, A. M., et al., *Arch. Dermatol.,* 88:702–05 (1963). The skin was positioned over an in vitro cell 10, containing a cathode 11. A constant DC current was supplied to the anode 12 and cathode 11. Receptor fluid 13 was supplied to the in vitro cell 10. The receptor fluid had the following composition:

| Water | 3 liters |
|---|---|
| 1N NaOH | 17.5 ml |
| PEG 400 | 70 ml |
| (Carbowax 400 NF, Union Carbide) | |
| Surfactant | 3 ml |
| (Pluronic P103, BASF P103) | |
| NaCl | 17.54 gm |
| Buffer HEPES | 7.15 gm |
| (N-[2-Hydroxyethyl]piperazine- | |
| N'-[2 ethanesulfonic acid]) Sigma | |
| Sodium azide | 0.306 gm |

The above ingredients were mixed to obtain a solution for use as a receptor fluid with a pH of 7.4.

After the current was turned on, and the drug began to be transported across the membrane 9, the receptor fluid 13 in the in vitro cell was removed on an hourly basis via a pump 14, situated outside the in vitro cell 10. The fluid was then collected in a fraction collector 15 and the amount of drug delivered was measured by radioactivity detection means, not shown, as a function of time.

Using the hydrogel formulations of the present invention, A1, A2, and A3, as previously described, a constant current of 250 microamps per square centimeter was applied for 24 hours. The in vitro delivery of the drug was then measured as flux, in micrograms per hour as a function of time. The results are shown in FIG. 3. These results demonstrate that hydrogel compositions in accordance with the claimed invention are capable of iontophoretic drug delivery.

It will be understood by one of ordinary skill in the art that many possible hydrogel reservoir compositions are possible in accordance with the present invention, and the invention is therefore not limited to those compositions shown in the example. Similarly, a wide variety of suitable polyelectrolytes are known to those skilled in the art, and the present invention is not limited to those specifically mentioned.

What I claim is:

1. A hydrogel reservoir containing an active electrode in a two compartment iontophoretic device, wherein said two compartments are situated on top of each other and are separated by a permeable means, and wherein said hydrogel reservoir is situated in one of said two compartments and comprises polyvinylpyrrolidone, a non cross-linked water soluble polyelectrolyte having a molecular weight of about 1,000 or greater and a polar solvent.

2. A hydrogel reservoir containing an active electrode in a two compartment iontophoretic device, wherein said two compartments are situated on top of each other and are separated by a permeable means, and wherein said hydrogel reservoir is situated in one of said two compartments and comprises a non cross-linked water soluble polyelectrolyte, a polar solvent and wherein the non cross-linked water soluble polyelectrolyte is sodium polystyrene sulfonate.

3. A hydrogel reservoir according to claim 2 which further comprises a matrix-forming material.

4. A hydrogel reservoir according to claim 3 wherein the matrix-forming material is a hydrophilic polymer.

5. A hydrogel reservoir according to claim 4 wherein the hydrophilic polymer is polyvinylpyrrolidone.

6. A hydrogel reservoir for use in an iontophoretic device comprising water, polyvinylpyrrolidone and a non cross-linked water soluble polyelectrolyte having a molecular weight of about 1,000 or greater.

7. A hydrogel reservoir for use in an iontophoretic device comprising water, a hydrophilic polymer and a non cross-linked water soluble polyelectrolyte wherein the non cross-linked water soluble polyelectrolyte is sodium polystyrene sulfonate.

8. A hydrogel reservoir containing an active electrode in a two compartment iontophoretic device, wherein said two compartments are situated on top of each other and are separated by a permeable means, and wherein said hydrogel reservoir is situated in one of said two compartments and comprises water, polyvinylpyrrolidone and non cross-linked water soluble sodium polystyrene sulfonate.

9. A hydrogel reservoir according to claim 8 containing about 15% polyvinylpyrrolidone and about 15% sodium polystyrene sulfonate.

* * * * *